(12) United States Patent
Yonekawa

(10) Patent No.: US 9,072,484 B2
(45) Date of Patent: Jul. 7, 2015

(54) RADIATION IMAGE CAPTURING SYSTEM

(75) Inventor: Hisashi Yonekawa, Hachioji (JP)

(73) Assignee: KONICA MINOLTA, INC. (JP)

( * ) Notice: Subject to any disclaimer, the term of this patent is extended or adjusted under 35 U.S.C. 154(b) by 233 days.

(21) Appl. No.: 13/597,661

(22) Filed: Aug. 29, 2012

(65) Prior Publication Data

US 2012/0321043 A1 Dec. 20, 2012

Related U.S. Application Data

(63) Continuation of application No. 12/993,308, filed as application No. PCT/JP2009/053879 on Mar. 2, 2009, now Pat. No. 8,295,439.

(30) Foreign Application Priority Data

May 20, 2008 (JP) ................................. 2008-131765
Jun. 3, 2008 (JP) ................................. 2008-145371

(51) Int. Cl.
*H05G 1/56* (2006.01)
*A61B 6/00* (2006.01)

(52) U.S. Cl.
CPC ................. *A61B 6/4283* (2013.01); *A61B 6/00* (2013.01); *A61B 6/4216* (2013.01); *A61B 6/4233* (2013.01); *A61B 6/4494* (2013.01); *A61B 6/467* (2013.01); *A61B 6/542* (2013.01); *A61B 6/56* (2013.01); *A61B 6/566* (2013.01)

(58) Field of Classification Search
CPC .......... A61B 6/00; A61B 6/566; A61B 6/467; H05G 1/02

USPC .................................................. 378/114–115
See application file for complete search history.

(56) References Cited

U.S. PATENT DOCUMENTS

| 8,295,439 B2 | 10/2012 | Yonekawa |
|---|---|---|
| 2002/0080918 A1* | 6/2002 | Sako .............................. 378/115 |
| 2004/0066900 A1 | 4/2004 | Motoki |
| 2004/0071263 A1 | 4/2004 | Motoki |
| 2008/0247513 A1 | 10/2008 | Amitani et al. |
| 2008/0317214 A1 | 12/2008 | Maack |
| 2010/0104065 A1 | 4/2010 | Eguchi |
| 2011/0110494 A1 | 5/2011 | Lee |
| 2012/0134474 A1 | 5/2012 | Duca et al. |

FOREIGN PATENT DOCUMENTS

| EP | 1099410 A1 | 5/2001 |
|---|---|---|
| EP | 1406197 A2 | 8/2003 |
| EP | 1416320 A2 | 5/2004 |

(Continued)

OTHER PUBLICATIONS

International Search Report for International Application No. PCT/JP2009/053879 with English translation mailed on Apr. 7, 2009.

(Continued)

*Primary Examiner* — Hoon Song
(74) *Attorney, Agent, or Firm* — Cantor Colburn LLP

(57) ABSTRACT

A radiation image capturing system including a CR cassette and a FPD cassette, and when the radiation image capturing is started without either of the cassettes being loaded, the radiation generating apparatus is set for the CR cassette and when the icon of the FPD cassette is selected, the radiation generating apparatus is set for the FPD cassette.

2 Claims, 10 Drawing Sheets

(56) References Cited

FOREIGN PATENT DOCUMENTS

| | | |
|---|---|---|
| JP | 9-73144 A | 3/1997 |
| JP | 2001-149358 A | 6/2001 |
| JP | 2002-156717 A | 5/2002 |
| JP | 2002336225 A | 11/2002 |
| JP | 2003-290184 A | 10/2003 |
| JP | 2005-114944 A | 4/2005 |
| JP | 200587612 A | 4/2005 |
| JP | 2005-121783 A | 5/2005 |
| JP | 2005-185765 A | 7/2005 |
| JP | 2006-43274 A | 2/2006 |
| JP | 2006-58124 A | 3/2006 |
| JP | 2006-116001 A | 5/2006 |
| JP | 2006-122722 A | 5/2006 |
| JP | 2006-122723 A | 5/2006 |

OTHER PUBLICATIONS

Extended European Search Report for Application No./Patent No. 09750403.9-1265/2277444; dated Sep. 23, 2011.
Office Action for U.S. Appl. No. 14/141,965, dated Mar. 21, 2014.
Japanese Office Action, Reasons for Refusal for corresponding Japanese Patent Application No. 2014-026102; date of mailing Nov. 4, 2014; with English translation.
United States Non Final Office Action corresponding to U.S. Appl. No. 14/141,965; Date of Mailing: Feb. 26, 2015.

* cited by examiner

FIG.3

| P1 | P2 | P3 | P4 | P5 | P6 | P7 | P8 |
|---|---|---|---|---|---|---|---|
| CAPTURING ORDER ID | PATIENT ID | PATIENT NAME | SEX | AGE | DEPARTMENT | CAPTURING BODY PART | CAPTURING DIRECTION |
| 001 | 100085 | A | MALE | 25 | SURGICAL DEPARTMENT | CHEST | SIDE L |
| 002 | 100085 | A | MALE | 25 | SURGICAL DEPARTMENT | CHEST | SIDE R |
| 003 | 100085 | A | MALE | 25 | SURGICAL DEPARTMENT | LEG | L |
| 004 | 100085 | A | MALE | 25 | SURGICAL DEPARTMENT | LEG | R |
| 005 | 100125 | B | FEMALE | 55 | GYNECOLOGICAL DEPARTMENT | BREAST | MLO-R |
| 006 | 100125 | B | FEMALE | 55 | GYNECOLOGICAL DEPARTMENT | BREAST | MLO-L |
| 007 | 100125 | B | FEMALE | 55 | GYNECOLOGICAL DEPARTMENT | BREAST | CC-L |
| 008 | 100125 | B | FEMALE | 55 | GYNECOLOGICAL DEPARTMENT | BREAST | CC-R |
| 009 | 100320 | C | MALE | 15 | SURGICAL DEPARTMENT | CHEST | FRONT |
| 010 | 100325 | D | MALE | 60 | SURGICAL DEPARTMENT | CHEST | FRONT |

PLEASE INPUT CAPTURING ORDER INFORMATION OF CAPTURING TO BE PERFORMED

| P1 | P2 | P3 | P4 | P5 | P6 | P7 | P8 |
|---|---|---|---|---|---|---|---|
| CAPTURING ORDER ID | PATIENT ID | PATIENT NAME | SEX | AGE | DEPARTMENT | CAPTURING BODY PART | CAPTURING DIRECTION |
| 001 | 100085 | A | MALE | 25 | SURGICAL DEPARTMENT | CHEST | SIDE L |
| 002 | 100085 | A | MALE | 25 | SURGICAL DEPARTMENT | CHEST | SIDE R |
| 003 | 100085 | A | MALE | 25 | SURGICAL DEPARTMENT | LEG | L |
| 004 | 100085 | A | MALE | 25 | SURGICAL DEPARTMENT | LEG | R |
| 005 | 100125 | B | FEMALE | 55 | GYNECOLOGICAL DEPARTMENT | BREAST | MLO-R |
| 006 | 100125 | B | FEMALE | 55 | GYNECOLOGICAL DEPARTMENT | BREAST | MLO-L |
| 007 | 100125 | B | FEMALE | 55 | GYNECOLOGICAL DEPARTMENT | BREAST | CC-L |
| 008 | 100125 | B | FEMALE | 55 | GYNECOLOGICAL DEPARTMENT | BREAST | CC-R |
| 009 | 100320 | C | MALE | 15 | SURGICAL DEPARTMENT | CHEST | FRONT |
| 010 | 100325 | D | MALE | 60 | SURGICAL DEPARTMENT | CHEST | FRONT |

ENTER ← h13
RETURN ← h14

| P1 | P2 | P3 | P4 | P5 | P6 | P7 | P8 | P9 |
|---|---|---|---|---|---|---|---|---|
| CAPTURING ORDER ID | PATIENT ID | PATIENT NAME | SEX | AGE | DEPARTMENT | CAPTURING BODY PART | CAPTURING DIRECTION | MODE OF CAPTURING |
| 001 | 100085 | A | MALE | 25 | SURGICAL DEPARTMENT | CHEST | SIDE L | SIMPLE |
| 002 | 100085 | A | MALE | 25 | SURGICAL DEPARTMENT | CHEST | SIDE R | SIMPLE |
| 003 | 100085 | A | MALE | 25 | SURGICAL DEPARTMENT | LEG | L | SIMPLE |
| 004 | 100085 | A | MALE | 25 | SURGICAL DEPARTMENT | LEG | R | SIMPLE |
| 005 | 100125 | B | FEMALE | 55 | GYNECOLOGICAL DEPARTMENT | BREAST | MLO-R | SIMPLE |
| 006 | 100125 | B | FEMALE | 55 | GYNECOLOGICAL DEPARTMENT | BREAST | MLO-L | SIMPLE |
| 007 | 100125 | B | FEMALE | 55 | GYNECOLOGICAL DEPARTMENT | BREAST | CC-L | SIMPLE |
| 008 | 100125 | B | FEMALE | 55 | GYNECOLOGICAL DEPARTMENT | BREAST | CC-R | SIMPLE |
| 009 | 100320 | C | MALE | 15 | SURGICAL DEPARTMENT | CHEST | FRONT | SIMPLE |
| 010 | 100325 | D | MALE | 60 | SURGICAL DEPARTMENT | CHEST | FRONT | DYNAMIC CAPTURING |

FIG.10

PLEASE INPUT CAPTURING ORDER INFORMATION OF CAPTURING TO BE PERFORMED

| CAPTURING ORDER ID | PATIENT ID | PATIENT NAME | SEX | AGE | DEPARTMENT | CAPTURING BODY PART | CAPTURING DIRECTION | MODE OF CAPTURING |
|---|---|---|---|---|---|---|---|---|
| 001 | 100085 | A | MALE | 25 | SURGICAL DEPARTMENT | CHEST | SIDE L | SIMPLE |
| 002 | 100085 | A | MALE | 25 | SURGICAL DEPARTMENT | CHEST | SIDE R | SIMPLE |
| 003 | 100085 | A | MALE | 25 | SURGICAL DEPARTMENT | LEG | L | SIMPLE |
| 004 | 100085 | A | MALE | 25 | SURGICAL DEPARTMENT | LEG | R | SIMPLE |
| 005 | 100125 | B | FEMALE | 55 | GYNECOLOGICAL DEPARTMENT | BREAST | MLO-R | SIMPLE |
| 006 | 100125 | B | FEMALE | 55 | GYNECOLOGICAL DEPARTMENT | BREAST | MLO-L | SIMPLE |
| 007 | 100125 | B | FEMALE | 55 | GYNECOLOGICAL DEPARTMENT | BREAST | CC-L | SIMPLE |
| 008 | 100125 | B | FEMALE | 55 | GYNECOLOGICAL DEPARTMENT | BREAST | CC-R | SIMPLE |
| 009 | 100320 | C | MALE | 15 | SURGICAL DEPARTMENT | CHEST | FRONT | SIMPLE |
| 010 | 100325 | D | MALE | 60 | SURGICAL DEPARTMENT | CHEST | FRONT | DYNAMIC CAPTURING |

RETURN     ENTER

RADIATION IMAGE CAPTURING SYSTEM

The present application is a continuation application of U.S. patent application Ser. No. 12/993,308, filed Nov. 18, 2010, the entire contents of which are incorporated herein by reference and priority to which is hereby claimed. application Ser. No. 12/993,308 is a U.S. National Stage Application of International Application PCT/JP2009/053879 filed Mar. 2, 2009, priority to which is claimed herein and the contents of which are incorporated herein by reference. The PCT/JP2009/053879 application claimed the benefit of the date of the earlier filed Japanese Patent Application Nos. JP2008-131765 filed May 20, 2008, and JP 2008-145371, filed Jun. 3, 2008, the entire contents of which are incorporated herein by reference, and priority which is hereby claimed.

TECHNICAL FIELD

The present invention relates to a radiation image capturing system.

BACKGROUND ART

Conventionally, radiation images captured using radiation as represented by an X-ray image are widely used for the purpose of diagnosis of disease, etc. Such medical radiation images were conventionally captured using screen/film. However, lately, digitalization of radiation images is realized, and for example, a CR (Computed Radiography) apparatus is widely used in which after radiation transmitted through an object is accumulated on a photostimulable phosphor sheet formed with a photostimulable phosphor layer, the photostimulable phosphor sheet is scanned with a laser beam and with this, photoelectric conversion is performed on the photostimulable luminescence emitted from the photostimulable phosphor sheet to obtain the image data.

In the radiation image capturing, a cassette (For example, see Patent Document 1-3. Hereinafter referred to as a "CR cassette".) with a storage medium such as a screen film, photostimulable phosphor sheet, etc. stored inside is used. The CR cassette is designed and manufactured according to size of the JIS (Japanese Industrial Standards) standard of the cassette for screen/film so that the CR cassette can be continuously used in an existing bucky device. In other words, the compatibility of the size of the cassette is maintained to achieve effective utilization of the facilities and digitalization of the image data.

Lately, as a method to obtain a medical radiation image, a FPD (Flat Panel Detector) is known as a detector to detect emitted radiation and to obtain digital image data (For example, see Patent Document 4.), and further a portable capturing apparatus (Portable FPD. Hereinafter, referred to as FPD cassette.) storing an FPD in a housing is put into practical use (For example, see Patent Document 5.).

In such FPD cassette, for example, a scintillator to convert the emitted radiation to light and a photoelectric conversion element such as a photodiode to convert the light to an electric signal are stored in a box (housing) and an electric signal accumulated in the photoelectric conversion element is read out to obtain image data.

Also, lately, a radiation image capturing system (For example, see Patent Document 6.) is known in which an environment with high work efficiency and ease of operation for a radiological technologist, doctor, etc. (Hereinafter referred to as an operator.) can be obtained where X-ray capturing apparatuses of different types with different detection sections are mixed and an image quality at a certain level can be obtained. Also, a radiation image capturing system (For example, see Patent Document 7.) is known to capture a moving image using a FPD cassette to capture a dynamic state of breathing of a chest of a human body.

Patent Document 1: Japanese Patent Application Laid-Open Publication No. 2005-121783
Patent Document 2: Japanese Patent Application Laid-Open Publication No. 2005-114944
Patent Document 3: Japanese Patent Application Laid-Open Publication No. 2002-156717
Patent Document 4: Japanese Patent Application Laid-Open Publication No. 9-73144
Patent Document 5: Japanese Patent Application Laid-Open Publication No. 2006-058124
Patent Document 6: Japanese Patent Application Laid-Open Publication No. 2001-149358
Patent Document 7: Japanese Patent Application Laid-Open Publication No. 2003-290184

DISCLOSURE OF THE INVENTION

Problems to be Solved by the Invention

As described above, the CR cassette currently widespread is a size according to the size of the JIS standard in a conventional screen/film cassette and the bucky device in which the cassette is loaded is also designed to match the size of the JIS standard. Therefore, if the FPD cassette is also configured in a shape stored in a cassette according to the size of the JIS standard, existing equipment in a facility can be used in capturing with the FPD cassette and equipment investment when the FPD cassette is installed as the capturing section can be kept to a minimum.

However, since the FPD cassette can detect a low dose of radiation more effectively than the CR cassette, there is a difference that emission amount of radiation emitted to an object (capturing object body part of a patient) from the radiation source of the radiation generating apparatus is usually set at a lower dose than that of the CR cassette. Therefore, when capturing can be performed using both of the CR cassette and the FPD cassette in the same bucky device as described above, when the operator starts the radiation generating apparatus associated with the bucky device, the operator needs to set a condition of the radiation generating apparatus such as emission amount of radiation depending on whether the cassette used is the CR cassette or the FPD cassette.

Also, when capturing is performed a plurality of times using the CR cassette or when moving image capturing in which the FPD cassette is used as described in Patent Document 7 is performed using the CR cassette by mistake, this results in multi-exposure so that the image cannot be used for diagnosis, and also increases total exposure amount due to capturing performed again. Therefore, when it is possible to perform capturing using both of the CR cassette and the FPD cassette in the same bucky device as described above, it is necessary to check whether or not the type of cassette to be used in capturing is suitable for capturing when the operator sets successive capturing or moving image capturing as a capturing condition.

However, it is troublesome for an operator to check type of cassette loaded on the bucky device based on the capturing order information or to set the emission condition of the radiation generating apparatus according to type of cassette loaded on the bucky device each time capturing is performed. Also, when capturing is performed with a capturing condition regarding a cassette of a type different from the type of cassette loaded on the bucky device, since suitable image data cannot be obtained, capturing needs to be performed again, and there is a problem that exposure amount increases on the patient as an object.

The present invention is conceived to solve the above problems, and an object of the present invention is to provide a radiation image capturing system in which an emission condition of the radiation generating apparatus associated with the bucky device can be appropriately set in an environment where capturing is possible by loading either the CR cassette or the FPD cassette on the same bucky device. Also, an object of the present invention is to provide a radiation image capturing system in which radiation image capturing with an unsuitable cassette can be automatically and accurately prevented when successive capturing or moving image capturing is set by the operator.

Means for Solving the Problem

In order to achieve the above object, according to the invention of claim 1, there is provided a radiation image capturing system including:

a radiation generating apparatus to emit radiation;

a bucky device associated with the radiation generating apparatus in advance;

a portable FPD cassette which can capture a plurality of radiation images of an object successively in a state loaded on the bucky device or by itself;

a CR cassette which can store a radiation image of an object in a state loaded on the bucky device or by itself; and a console including a display section to display each icon corresponding to each of the usable bucky device and portable FPD cassette, the console which can communicate with the bucky device, the portable FPD cassette, and the radiation generating device, wherein the bucky device notifies the console the type of cassette loaded when either one of the cassette of the portable FPD cassette or the CR cassette is loaded; and when the icon corresponding to the bucky device is selected from the icon displayed on the display section, the console starts the radiation generating apparatus associated with the selected bucky device and controls the radiation generating apparatus to emit radiation from the radiation generating apparatus with a different emission amount according to the type of the loaded cassette notified from the bucky device.

Preferably, according to the invention of claim 2, there is provided the radiation image capturing system of claim 1, wherein the console displays the icon corresponding to the bucky device in a different manner according to whether or not the portable FPD cassette is loaded on the bucky device based on the notification and to control the radiation generating apparatus to emit radiation from the radiation generating apparatus with a different emission amount according to whether or not the portable FPD cassette is loaded on the bucky device.

Preferably, according to the invention of claim 3, there is provided the radiation image capturing system of claim 2, wherein when the icon corresponding to the portable FPD cassette is selected in a state where another icon corresponding to the bucky device in which the portable FPD cassette is not loaded is selected, the console controls the radiation generating apparatus associated with the bucky device to emit radiation of an emission amount to be emitted when the portable FPD cassette is loaded on the bucky device.

Preferably, according to the invention of claim 4, there is provided the radiation image capturing system of claim 2 or 3,
wherein when the icon corresponding to the portable FPD cassette is not selected after a predetermined amount of time passes in a state where another icon corresponding to the bucky device in which the portable FPD cassette is not loaded is selected, the console controls the radiation generating apparatus associated with the bucky device to emit radiation of an emission amount to be emitted when the CR cassette is loaded on the bucky device.

Preferably, according to the invention of claim 5, there is provided the radiation image capturing system of any one of claims 1 to 4, further including, a storage section to store capturing order information including information of a patient to be an object of radiation image capturing and capturing condition, wherein the console obtains at least one piece of the capturing order information from the storage section to display on the display section and when one piece of the capturing order information is selected, the console displays the icon on the display section.

Preferably, according to the invention of claim 6, there is provided the radiation image capturing system of claim 5 wherein the console adjusts the emission amount of radiation emitted from the radiation generating apparatus associated with the bucky device corresponding to the selected icon based on the capturing condition included in the selected capturing order information.

Preferably, according to the invention of claim 7, there is provided the radiation image capturing system of any one of claims 1 to 6, wherein the console includes a warning section to give a warning when the icon is displayed and an icon corresponding to the bucky device is selected from the icon, but the type of cassette loaded on the selected bucky device and the set capturing condition do not match.

Preferably, according to the invention of claim 8, there is provided the radiation image capturing system of claim 7, further including, a storage section to store capturing order information including the capturing condition, wherein the console includes a warning section to give a warning, wherein the console obtains at least one piece of the capturing order information from the storage section to display on the display section, and when one piece of the capturing order information is selected, the console displays the icon and when the icon corresponding to the bucky device is selected from the icon, the warning section gives a warning when the type of cassette loaded on the selected bucky device and the capturing condition set in the capturing order information do not match.

Preferably, according to the invention of claim 9, there is provided the radiation image capturing system of claim 7 or 8 wherein the warning section is provided in the console.

Preferably, according to the invention of claim 10, there is provided the radiation image capturing system of any one of claims 7 to 9 wherein the bucky device includes the warning section.

Advantageous Effect of the Invention

According to the invention described in claim 1, in a capturing environment where, for example, by forming both of the FPD cassette and the CR cassette in a JIS standard size of the screen/film cassette, both the FPD cassette and the CR cassette can be loaded on the same bucky device, the operator such as the radiological technologist, doctor, etc., does not have to set the emission condition of the radiation generating apparatus according to the type of cassette loaded on the bucky device and the emission condition can be automatically and suitably set by simply performing the icon operation on the screen of the display section of the console.

Therefore, the operation of the radiation image capturing becomes very easy, and at the same time it is possible to effectively prevent the operator from setting the capturing condition of a type of cassette different from the type of cassette loaded on the bucky device, and it is possible to effectively prevent the total exposure amount of the patient from increasing by performing capturing again. Also, by beginning the starting of the radiation generating apparatus associated with the bucky device immediately at the step when the bucky device is selected by icon operation on the screen of the display section of the console, the radiation image capturing can begin promptly.

According to the invention described in claim 2, in addition to the above advantageous effects, by displaying the icon in a different manner according to whether or not the portable FPD cassette is loaded on the bucky device, the operator can easily confirm whether the portable FPD cassette is loaded on the bucky device properly and it is possible to accurately prevent incorrect operation by the operator.

According to the invention described in claim 3, in addition to the above advantageous effects, even when the portable FPD cassette is not loaded on the bucky device at the time of icon selection, when the FPD cassette is selected by icon operation, it should be recognized as to be used by loading on the bucky device of selected, and it is possible to easily control the radiation generating apparatus to emit radiation of an emission amount to be emitted when the portable FPD cassette is loaded on the bucky device and it is possible to easily perform change of emission amount.

According to the invention described in claim 4, in addition to the above advantageous effects, when the portable FPD cassette is not presently loaded on the bucky device, and the portable FPD cassette is not selected by icon operation, it is possible to control the radiation generating apparatus to emit radiation of an emission amount to be emitted when the CR cassette is loaded on the bucky device, and it is possible to easily and promptly perform starting of the radiation generating apparatus.

According to the invention described in claim 5, in addition to the above advantageous effects, the console can perform the starting of the radiation generating apparatus promptly and accurately based on the selected capturing order information.

According to the invention described in claim 6, in addition to the above advantageous effects, it is possible to make suitable fine adjustments of the emission amount of radiation to be emitted from the radiation generating apparatus to the patient, whether the patient is an adult or a child, whether the patient is fat or thin, etc. and it is possible to decrease the exposure amount of the patient.

According to the invention described in claim 7, in addition to the above advantageous effects, in an environment where, for example, by forming both of the CR cassette and the FPD cassette in a JIS standard size of the screen/film cassette, it is possible to capture by loading either the CR cassette or the FPD cassette on the same bucky device, in a case where a capturing condition such as successive capturing, moving image capturing, etc. is set by the operator when the CR cassette is loaded on the bucky device, or a capturing condition for the CR cassette is set but the FPD cassette is loaded on the bucky device, it is possible to judge that the type of cassette loaded on the selected bucky device does not match the set capturing condition and a warning can be made.

Therefore, the operation of the radiation image capturing becomes very easy and at the same time, when the type of cassette loaded on the selected bucky device does not match the set capturing condition, it is possible to automatically and accurately prevent radiation image capturing from being performed using an unsuitable cassette, and it is possible to effectively prevent the total exposure amount of the patient from increasing by performing capturing again.

According to the invention described in claim 8, in addition to the above advantageous effects, since the capturing condition is set in the capturing order information in advance, it is possible to judge whether or not the type of cassette loaded on the selected bucky device matches the set capturing condition at the step of when the icon displayed on the display section of the console is clicked and selected, and when there is no match, it is possible to immediately give a warning from the warning section.

According to the invention described in claim 9, by providing a warning section in the console, it is possible to accurately give a warning to the operator operating the console to transmit that the type of cassette loaded on the selected bucky device does not match the set capturing condition to raise attention and it is possible to realize the above advantageous effects more accurately.

According to the invention described in claim 10, by providing a warning section in the bucky device, it is possible to accurately give a warning to the operator operating the bucky device, etc. to transmit that the type of cassette loaded on the selected bucky device does not match the set capturing condition to raise attention and it is possible to realize the above advantageous effects more accurately.

BRIEF DESCRIPTION OF THE DRAWINGS

FIG. 3 is a diagram showing an example of capturing order information;

FIG. 4 is a diagram showing an example of a selected image displayed with capturing order information displayed on a display section of a console;

FIG. 9 is a diagram showing an example of the capturing order information according to the third embodiment; and FIG. 10 is a diagram showing an example of a selected image displayed with the capturing order information displayed on the display section of the console according to the third embodiment.

BEST MODE FOR CARRYING OUT THE INVENTION

Below, an embodiment of a radiation image capturing system of the present invention is described with reference to the drawings. However, the present invention is not limited to the illustrated examples below.

First Embodiment

Figure 1:
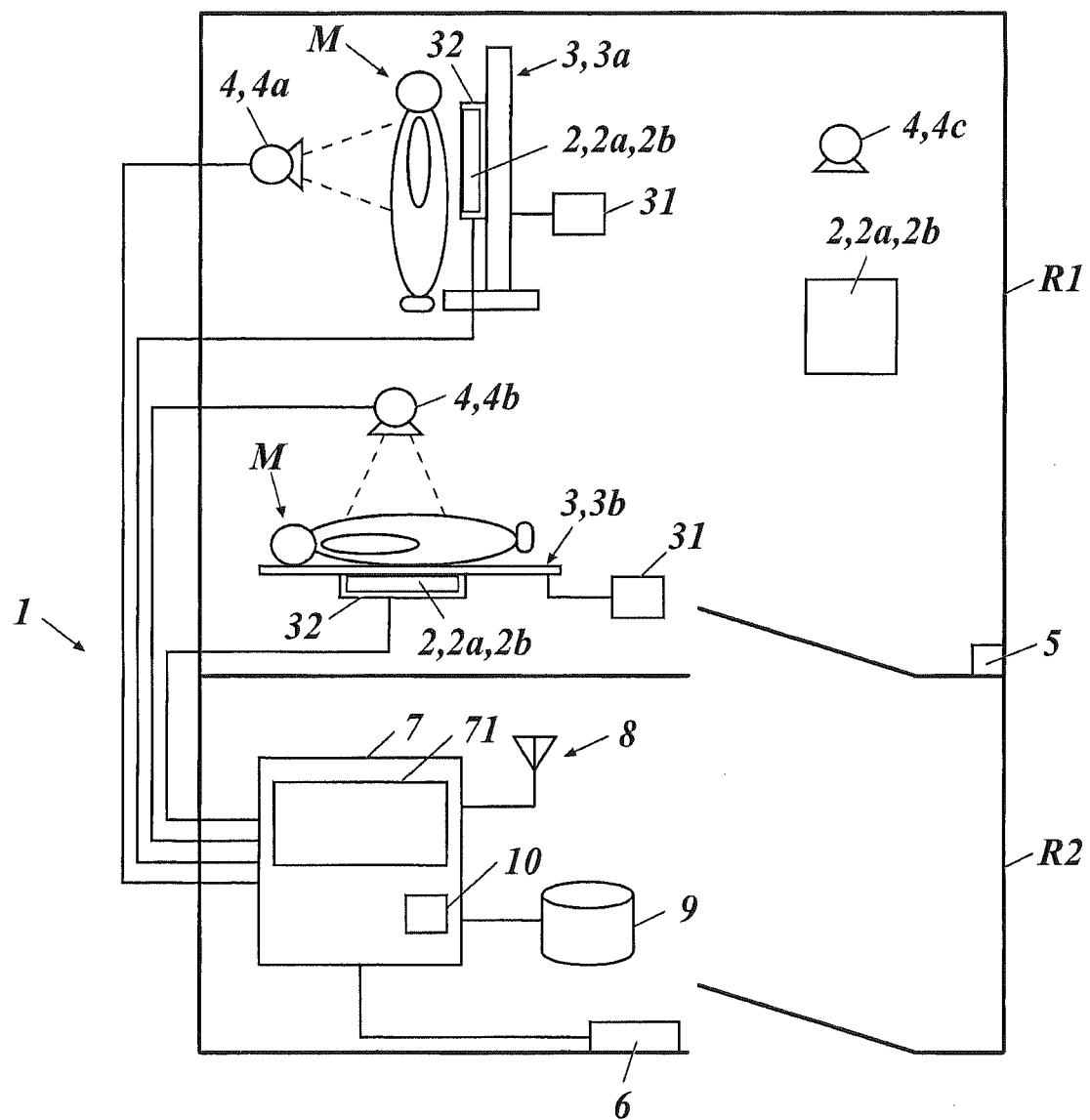
FIG. 1 is a diagram showing an entire configuration of a radiation image capturing system.

The first embodiment of the radiation image capturing system 1 is a system assuming radiation image capturing performed in a hospital or clinic, and as shown in FIG. 1, for example, the system is provided in a capturing room R1 to emit radiation to perform capturing of an object (capturing object body part of a patient M) which is a portion of the patient M, and a front room R2 for an operator to control radiation emitted on the object, or to perform image processing, etc. on the radiation image obtained by emitting radiation.

In the present embodiment, the capturing room R1 is provided with a bucky device 3 in which a portable FPD cassette 2*a* and CR cassette 2*b* can be loaded, a radiation generating apparatus 4 provided with a radiation source such as an X-ray tube to emit radiation on the object, a wireless access point (base station) 5, etc. to relay communication when the wireless communication is performed between the FPD cassette 2*a* and a console 7.

Also, the front room R2 is provided with a tag reader 6 to detect the later described tag embedded in the FPD cassette 2*a* and the console 7 to perform control of the entire radiation image capturing system 1. In the present embodiment, the radiation image capturing system 1 is provided with at least the bucky device 3, the radiation generating apparatus 4, the FPD cassette 2*a*, the CR cassette 2*b*, a reading device for the CR cassette which is not shown, and the console 7. Below, the FPD cassette 2*a* and the CR cassette 2*b* are generally referred to as cassette 2.

Among the cassette 2, although illustration is omitted, as the CR cassette 2*b*, a configuration where the photostimulable phosphor sheet as described in, for example, above described patent document 3 is sandwiched between a front board and a back board is used. In the present embodiment the CR cassette 2*b* is configured in a dimension complying with JIS Z 4905 (corresponding international standard is IEC 60406) of a conventional screen/film cassette.

In other words, the thickness in the entering direction of radiation is formed within a range of 15 mm+1 mm to 15 mm−2 mm, and the cassette is prepared in a size of 8 inch×10 inch, 10 inch×12 inch, 11 inch×14 inch, 14 inch×14 inch, 14 inch×17 inch, 17 inch×17 inch, etc.

Also, a barcode label printed with an optically readable pattern is printed or applied on a predetermined position on a back face (face on the opposite side of the face of the side where radiation enters) of the CR cassette 2*b*. Unique information of the CR cassette 2*b* is stored in the barcode label and the unique information includes for example, cassette ID as identification information assigned to the CR cassette 2*b*, size information etc.

When the radiation image capturing is performed using the CR cassette 2*b*, reading of a signal from the photostimulable phosphor sheet, etc. by the reading device which is not shown is necessary, and after the radiation image of the object is captured, the operator brings the CR cassette 2*b* in a later described state of being loaded on the bucky device 3 or by itself (not loaded on the bucky device) to the reading device and performs reading processing.

Figure 2:
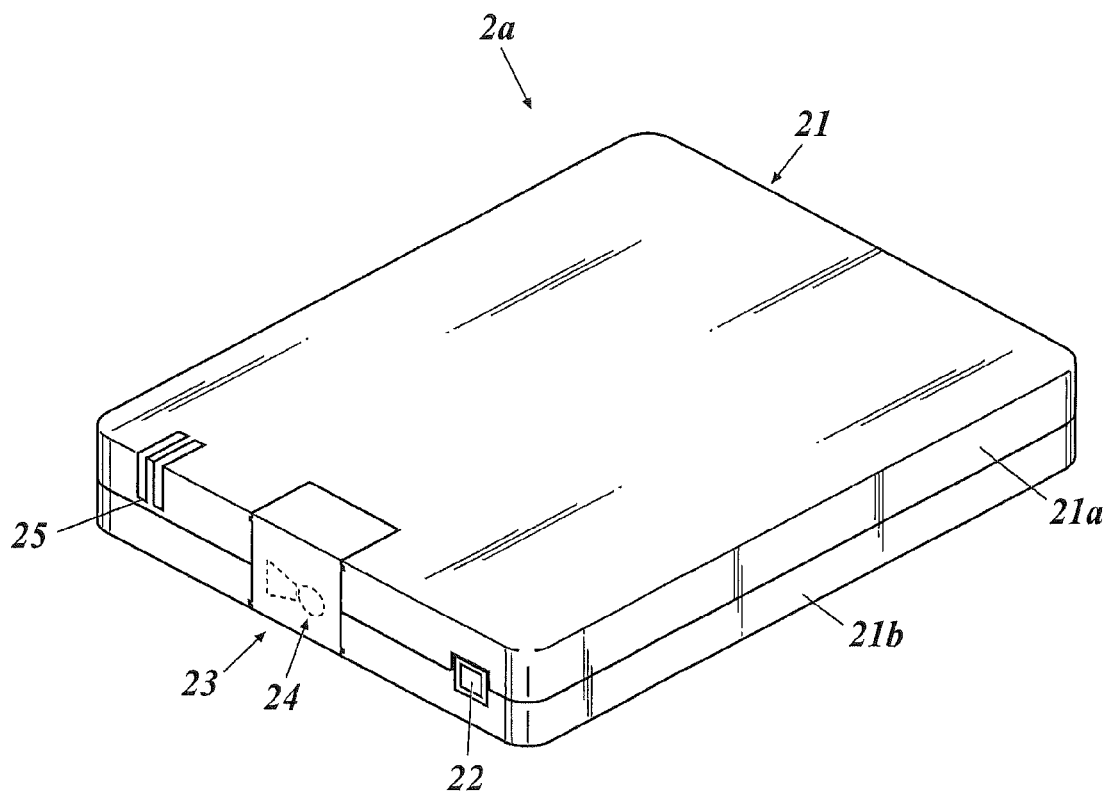
FIG. 2 is a perspective diagram showing an outer configuration of the FPD cassette.

Among the cassette 2, as shown in FIG. 2, as the FPD cassette 2*a*, a box 21 in which a radiation detection panel is embedded can be used, and the radiation detection panel includes a scintillator and a photoelectric conversion element such as a photodiode aligned two dimensionally, which is not shown. The type of radiation detection panel is not limited to the above type, and various types can be used such as a direct type, as it is called, to directly detect the radiation with radiation detecting elements. Also, FIG. 2 shows the box 21 formed with a front member 21*a* and a back member 21*b*, however, besides this, the box 21 can be formed in a monocoque shape of a pipe shape.

Also, in the present embodiment, in the side face portion of the FPD cassette 2*a*, a power source switch 22 is provided to switch power of the FPD cassette 2*a* to ON/OFF. Also, the side face portion of the FPD cassette 2*a* is provided with a cover member 23 to open and close for changing a rechargeable battery which is not shown embedded in the box 21, and on the side face section of the cover member 23, an antenna device 24 is embedded for the FPD cassette 2*a* to perform transmitting and receiving of information wireless with external sections through the wireless access point 5. Also, in the side face portion, an indicator 25 is provided configured with, for example, an LED to display charged state of the rechargeable battery and various operation status, etc.

Further, on the side face portion on the opposite side of the side face portion of the FPD cassette 2*a* on which the power source switch 22 is provided, a terminal which is not shown is provided to be connected to an electrode in the bucky device 3 which is not shown so that the FPD cassette 2*a* receives supply of electric power from an external section and transmits and receives a signal with the external section through the bucky device 3 when the FPD cassette 2*a* is loaded on the bucky device 3.

Also, a tag which is not shown is embedded in the FPD cassette 2*a*. In the present embodiment, a tag which is called an RFID (Radio Frequency Identification) tag is used and a control circuit to control each section of the tag and a storage section to store the unique information of the FPD cassette 2*a* are embedded compactly in the tag.

The FPD cassette 2*a* is configured so that when the FPD cassette 2*a* receives an electric wave (request signal) sent out from the tag reader 6 through the antenna device 24, the unique information stored in the storage section of the tag is sent to the tag reader 6 through the antenna device 24. The unique information includes, for example, cassette ID as identification information assigned to the FPD cassette 2*a*, and type information, size information, and resolution of the scintillator. The thickness and the size of the FPD cassette 2*a* are similar to those of the CR cassette 2*b*, and is configured in a size complying with JIS Z 4905 (corresponding international standard is IEC 60406).

In the present embodiment, the FPD cassette 2*a* and the CR cassette 2*b* can be used loaded on the bucky device 3, or can be used by itself. In other words, the cassette 2 (FPD cassette 2*a* and CR cassette 2*b*) can be used without loading in the bucky device 3, and placed in an uncovered state and then a hand, etc. of the patient M as an object is placed on the upper face (face on the side where radiation enters) and radiation is emitted from a portable radiation generating apparatus 4*c*, in other words, a free radiation generating apparatus which is not associated with the bucky device 3 to obtain image data.

As described above, when the capturing is performed with the FPD cassette 2*a* loaded on the bucky device 3, the FPD cassette 2*a* receives supply of electric power from the external section through the bucky device 3 through the previously described terminal and performs transmitting and receiving of signal with the external section such as transmission of image data, alternatively, when the FPD cassette 2a is used by itself, the FPD cassette 2a operates by electric power of the embedded rechargeable battery and transmitting and receiving of a signal such as transmission of image data with the external section, especially with the console 7 is performed by wireless communication via the wireless access point 5 provided in the capturing room R1 through the antenna device 24 of the FPD cassette 2a. For example, another possible configuration is to bring the FPD cassette 2a to the front room R2 to connect to the console 7 to transmit the image data to the console 7.

Also, the FPD cassette 2a is embedded with a storage section which is not shown and each image data obtained by the plurality of radiation image capturing can be stored temporarily. Therefore, the FPD cassette 2a can be used to emit radiation successively on the object and to store the image data each time in order to perform successive capturing or moving image capturing.

The capturing room R1 is shielded with lead, etc. so that the radiation does not leak outside. As a device to hold the cassette 2 to perform the radiation image capturing, the capturing room R1 is provided with the bucky device 3. In the present embodiment, as the bucky device 3, a bucky device 3a for capturing in a standing position and bucky device 3b for capturing in a lying position are each provided.

The bucky device 3 is provided with an operation section 31 including a monitor which is not shown such as a CRT (Cathode Ray Tube) or LCD (Liquid Crystal Display), an operation input section such as a keyboard or a touch panel, an audio section, a CPU (Central Processing Unit), etc. The monitor of the operation section 31 displays information such as patient information, capturing condition, etc. sent from the console 7 and the operator looks at the display to check the patient, capturing body part, etc.

The bucky devices 3 are each provided with a cassette holding section 32 to hold the cassette 2 in a predetermined position and in the present embodiment, either one of the FPD cassette 2a or the CR cassette 2b each formed in the JIS standard size of the screen/film cassette can be loaded on each cassette holding section 32 of the bucky devices 3a and 3b for capturing in a standing position and capturing in a lying position.

Although not shown, the cassette holding section 32 of the bucky device 3 is provided with a loading detection device such as a micro switch to physically detect the cassette 2 is loaded, an electrode to connect to the terminal of the FPD cassette 2a when the FPD cassette 2a is properly loaded, a barcode reader to optically read a barcode of the CR cassette 2b when the CR cassette 2b is loaded, and the like.

Then, when the barcode of the CR cassette 2b cannot be read by the barcode reader and communication with the FPD cassette 2a is not established through the electrode even when the loading detection device detects loading of the cassette 2 on the cassette holding section 32, the audio section of the operation section 31 gives a warning to the operator to raise attention.

This is because these are cases such as the power source of the FPD cassette 2a loaded on the cassette holding section 32 of the bucky device 3 is not turned ON, the FPD cassette 2a is loaded to the cassette holding section 32 from the side face portion of the side on which the terminal of the FPD cassette 2a is not provided, in other words, the side face portion on the side where the antenna device 24 is provided or the cassette 2 is loaded with the front and back backwards and in all cases the cassette 2 needs to be loaded again.

When the bucky device 3 detects either the FPD cassette 2a or the CR cassette 2b is properly loaded based on the signal from the loading detection device, electrode, barcode reader, etc., the bucky device 3 notifies the console 7 that the device is in the cassette loaded status.

The detection of the loading of the FPD cassette 2a is performed by the above described, detection of signal from the electrode, detection of physical connection to the communication connector section not shown, detection of gloss of outer surface of the FPD cassette 2a, detection of power source level of the FPD cassette 2a, communication from the antenna device 24 to the wireless port not shown provided in the bucky device 3, detection of a signal from an RFID, etc. Alternatively, the detection of the loading of the CR cassette 2b is performed based on a signal from the barcode reader, etc. The bucky device 3 notifies the type (FPD or CR) of the loaded cassette 2, the ID of the cassette, etc.

In the present embodiment, the operator can operate the operation section 31 through the operation input section only when the bucky device 3 detects the cassette 2 is loaded properly. In other words, the operation section 31 does not receive operation as long as the cassette 2 is not properly loaded on the bucky device 3.

Similar to well known bucky devices, for example, the position adjustment of the bucky device itself, the adjustment of the height of the cassette holding section 32 with respect to the device main body, etc. can be performed as necessary in the bucky device 3a for capturing in a standing position and the bucky device 3b for capturing in a lying position.

The capturing room R1 is provided with at least one radiation generating apparatus 4 provided with a radiation source to emit radiation to the object. In the present embodiment, the bucky devices 3a and 3b for capturing in a standing position and capturing in a lying position are each associated with radiation generating apparatuses 4a and 4b in advance and these devices are provided in the capturing room R1. In the present embodiment, it is possible to provide one radiation generating apparatus associated with both bucky devices 3a and 3b for capturing in a standing position and capturing in a lying position.

In the present embodiment, the portable radiation generating apparatus 4c which is not associated with any of the bucky device 3a for capturing in a standing position and the bucky device 3b for capturing in a lying position is provided and the portable radiation generating apparatus 4c is portable anywhere in the capturing room R1 and can emit radiation to any direction.

In the present embodiment, the portable radiation generating apparatus 4c is not under control of the console 7, and when used with the FPD cassette 2a, the portable radiation generating apparatus 4c is turned on with a wireless signal from the FPD cassette 2a and when used with the CR cassette 2b, the portable radiation generating apparatus 4c is turned on manually by the operator, however, a configuration where the portable radiation generating apparatus 4c is turned on by operation of the console 7 is possible.

The radiation generating apparatus 4 includes an X-ray tube as a radiation source, and when high voltage is applied to the X-ray tube, an amount of radiation according to the voltage is emitted. The bucky device 3a for capturing in a standing position which is associated to the radiation generating apparatus 4a and the bucky device 3b for capturing in a lying position which is associated to the radiation generating apparatus 4b are for example, provided hanging down from the ceiling of the capturing room R1 and are turned on based on an instruction from the console 7 at time of capturing, and is moved to a predetermined position with a moving section which is not shown and this point is described in detail below.

The wireless access point (base station) 5 to relay communication when the FPD cassette 2a and the console 7 communicate wireless is provided in a corner of the capturing room R1. FIG. 1 shows the wireless access point 5 provided near the entrance of the capturing room R1, however, the embodiment is not limited to this, and the wireless access point 5 is provided suitably where wireless communication is possible with the wireless communication section 8 of the console 7.

The tag reader 6 to transmit and receive information with the FPD cassette 2a using RFID technology is provided near the entrance of the front room R2. The tag reader 6 places predetermined instruction information on the electric wave, etc. and transmits the information through the embedded antenna which is not shown, and detects the FPD cassette 2a which enters or exits the front room R2, in other words, detects the FPD cassette 2a which enters into a predetermined range of the capturing room R1 and the front room R2 and reads the unique information stored in the RFID tag of the FPD cassette 2a to transmit the read unique information to the console 7.

The front room R2 is provided with the console 7. The console 7 is configured with a computer in which a CPU, ROM (Read Only Memory), RAM (Random Access Memory), input/output interface which are not shown are connected to each other through a bus. A predetermined program stored in the ROM is read out to the work area of the RAM to be expanded and various processing is performed according to the program to control the entire radiation image capturing system 1 as described above. The console 7 is provided with a display section 71 such as a CRT or LCD and an input section which is not shown such as a keyboard or mouse is connected to the console 7.

The console 7 manages the FPD cassette 2a in the capturing room R1 and the front room R2 based on the unique information transmitted from the tag reader 6.

The bucky devices 3a and 3b for capturing in a standing position and capturing in a lying position, radiation generating apparatuses 4a and 4b associated to the bucky devices 3a and 3b, the portable radiation generating apparatuses 4c, the tag reader 6, etc. are each connected to the console 7 through a cable, etc., and the wireless communication section 8 to perform wireless communication with the FPD cassette 2a through the wireless access point 5 is connected to the console 7. It is possible to attach an antenna not shown to the wireless access point 5 to perform wireless communication with the FPD cassette 2a and to connect the wireless access point 5 to the console 7 with a wired line so that wired communication is performed in the communication between the wireless access point 5 and the console 7.

A storage section 9 configured with a hard disk, etc. is connected to the console 7. The storage section 9 stores information of the patient who is the object of radiation image capturing in the capturing room R1 and capturing order information including capturing condition. The capturing order information is input in the storage section 9 in advance in a list form before the radiation image capturing.

In the present embodiment, as shown in FIG. 3, the capturing order information is configured with, "patient ID" P2, "patient name" P3, "sex" P4, "age" P5, and "department" P6 as patient information, and "capturing body part" P7, "capturing direction" P8 as capturing information. Then, the "capturing order ID" P1 is automatically assigned to each capturing order information in the order the capturing order is received.

The content of the patient information and the capturing information written in the capturing order information is not limited to the above, and can be configured to include information such as year and date of birth of the patient, number of times of examination, amount of radiation, whether the patient is fat or thin, and the information can be set as necessary. Also, for example, the console 7 can connect to HIS (Hospital Information System) or RIS (Radiology Information System) through a network and obtain capturing order information from these systems.

The storage section 9 of the console 7 stores in advance a table in which the cassette ID is associated with type information, size information, information such as resolution of the scintillator for the FPD cassette 2a and the CR cassette 2b which can be used in the radiation image capturing in the capturing room R1.

Although not shown in FIG. 1, for example, an imager, which outputs visible film image based on the image data output from the console 7, is connected if necessary.

Below, the screen etc. displayed on the display section 71 of the console 7 is shown to describe the control of the radiation generating apparatus 4, etc. by the console 7 and to describe the operation of the radiation image capturing system of the present embodiment.

First, when the FPD cassette 2a is brought into outside to the front room R2 and the capturing room R1, the tag reader 6 provided near the entrance of the front room R2 reads the unique information stored in the RFID tag of the FPD cassette 2a and transmits the read unique information to the console 7. When the FPD cassette 2a is taken out of the capturing room R1 and front room R2, the tag reader 6 transmits the read unique information of the FPD cassette 2a to the console 7.

Then, the console 7 stores and registers in the memory such as the RAM, the cassette ID of the FPD cassette 2a which is brought into and deletes registration of the FPD cassette 2a taken out to know which FPD cassette 2a is still in the capturing room R1 and the front room R2.

When the cassette 2 (FPD cassette 2a or CR cassette 2b) is properly loaded on the bucky device 3 and the bucky device 3 notifies that the device is in the cassette loaded status, the console 7 associates the ID of the notifying bucky device 3 with the cassette ID, etc. of the loaded cassette 2 and stores and registers the above association.

When the radiation image is captured, the console 7 reads out the capturing order information stored in the storage section 9 (or obtains the capturing order information from the HIS/RIS through the network) and for example, as shown in FIG. 4, displays the information on the selection screen H1 of the display section 71.

In the present embodiment, a capturing order information display column h11 is provided in the selection screen H1 to display a list of the capturing order information stored in the storage section 9. On the left side of the capturing order information display column h11, a selection button h12 is provided corresponding to each piece of capturing order information to select capturing order information of the capturing to be performed this time. An enter button h13 and return button h14 are provided on the bottom side of the capturing order information display column h11.

Figure 5:
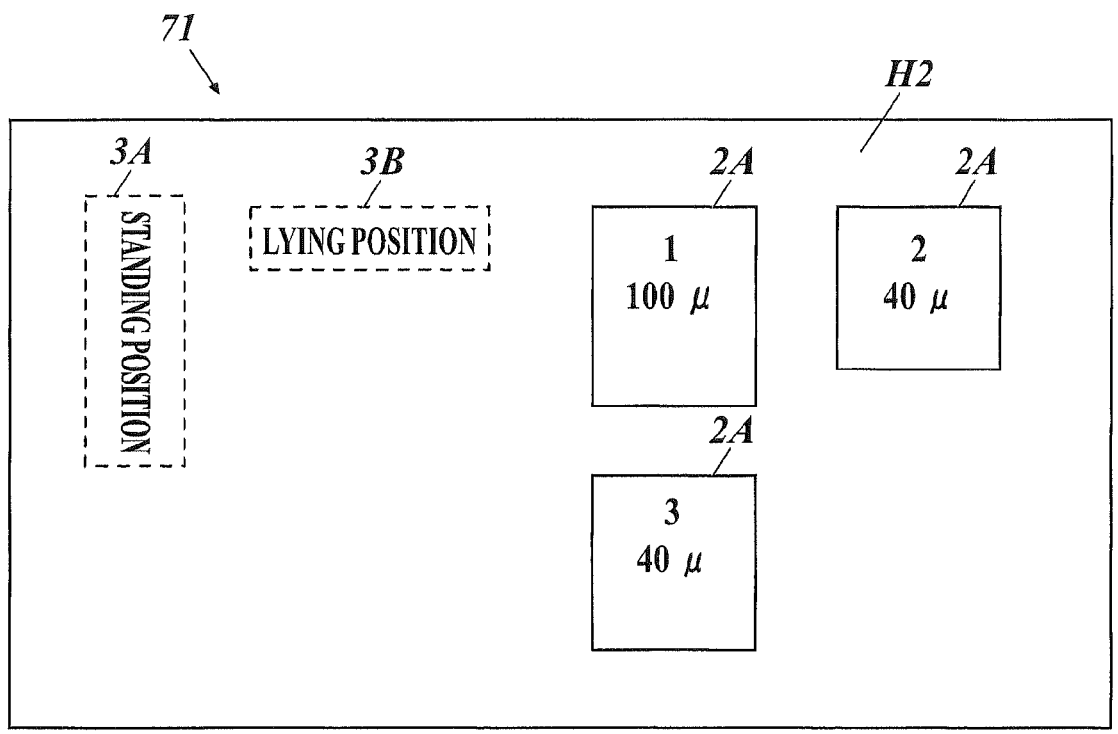
FIG. 5 is a diagram showing an example of a selected image displayed with an icon of the bucky device and the FPD cassette displayed on the display section of the console according to the first embodiment.
Figure 6:
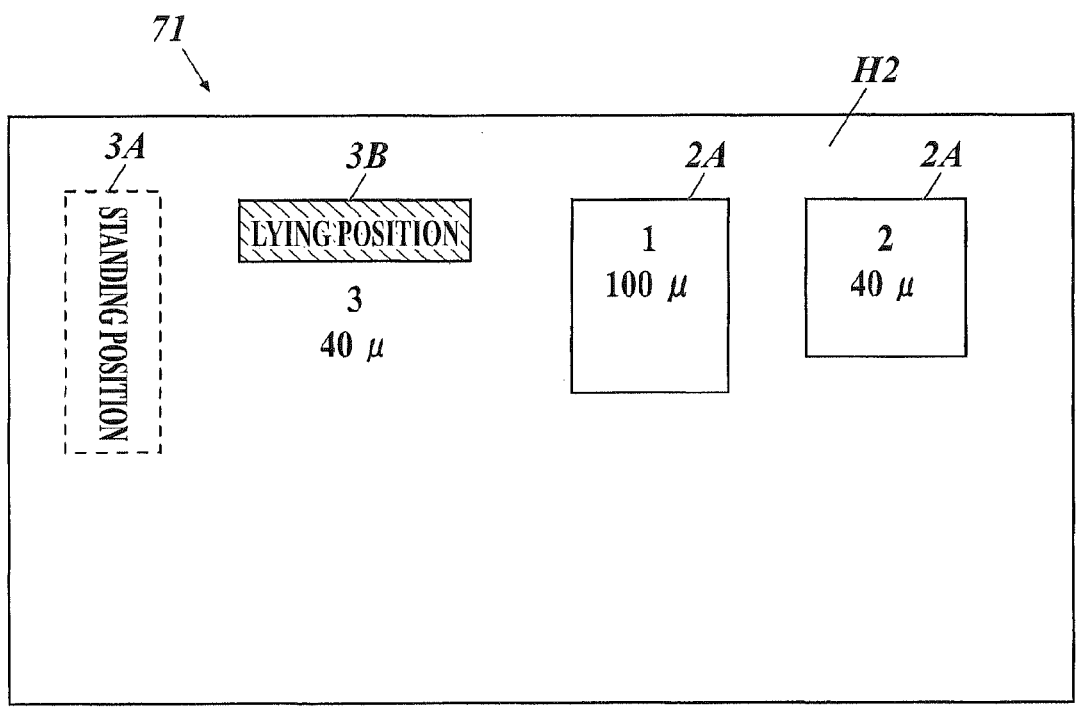
FIG. 6 is a diagram showing an example of a selected image displayed with the icon of the bucky device and the FPD cassette displayed on the display section of the console according to the first embodiment.

Then, when the capturing order information of the capturing to be performed this time is selected by clicking the selection button h12 corresponding to the capturing order information and clicking the enter button h13, the screen of the display section 71 is switched and next, the console 7 displays an icon as shown in, for example, FIG. 5 and FIG. 6 on the selection screen H2 of the display section 71.

In the present embodiment, as shown in FIG. 5 and FIG. 6, on the left side of the selection screen H2, icons 3A and 3B corresponding to the bucky device 3a for capturing in a standing position and the bucky device 3b for capturing in a lying position are each displayed in a state where the descriptions of "standing position" and "lying position" are surrounded by a rectangular border line. On the right side of the selection screen H2, icons 2A corresponding to the FPD cassettes 2a in the capturing room R1 and the front room R2 are displayed in a rectangular border line with a number 1 to 3 attached to each icon 2A.

In the present embodiment, the console 7 refers to the memory and when the cassette ID of the cassette 2 is not associated to the ID of the bucky device 3, the border line of the icon corresponding to the bucky device 3 is displayed with a broken line (see "standing position" 3A and "lying position" 3B shown in FIG. 5 and "standing position" 3A shown in FIG. 6) and displays at least the FPD cassette 2a is not loaded on the bucky device 3.

Also, when the cassette ID of the cassette 2 is associated with the ID of the bucky device 3, the border line of the icon corresponding to the bucky device 3 is displayed with a solid line and the inside of the border line is displayed colored with a predetermined color (see "lying position" 3B of FIG. 6) to display that the FPD cassette 2a is loaded on the bucky device 3. In FIG. 6, the number, resolution, etc. of the FPD cassette 2a loaded on the bucky device 3b for capturing in a lying position are displayed near the icon 3B of the "lying position".

As described above, in the present embodiment, the console 7 displays each icon corresponding to the bucky device 3 displayed on the display section 71 in a different manner according to whether or not the FPD cassette 2a is loaded on the bucky device 3 based on the notification from the bucky device 3.

Also, the console 7 refers to the memory and reads out the information such as resolution associated to each cassette ID of the FPD cassette 2a in the capturing room R1 and the front room R2, associates the number (1 to 3 shown in FIG. 5 and FIG. 6) attached to each cassette ID with the information such as resolution, etc. and displays the above information in the border line of the icons 2A corresponding to the FPD cassettes 2a displayed on the right side of the selection screen H2. It is possible to configure to further display the size, etc. of the FPD cassettes 2a.

For example, in a case where the operator loads the FPD cassette 2a with the number 3 on the bucky device 3b for capturing in a lying position and performs radiation image capturing, when the FPD cassette 2a with the number 3 is loaded on the bucky device 3b for capturing in a lying position in a state where the selection screen H2 shown in FIG. 5 is displayed, the selection screen H2 switches from the selection screen H2 shown in FIG. 5 to selection screen H2 shown in FIG. 6. If the FPD cassette 2a with the number 3 is loaded on the bucky device 3b for capturing in a lying position in advance, the selection screen H2 shown in FIG. 6 is displayed from the beginning when the selection screen H1 shown in FIG. 4 is switched to the selection screen H2.

In this state, for example, when the selection screen H2 shown in FIG. 6 is displayed and the icon 3B corresponding to the bucky device 3b for capturing in a lying position displayed with a solid line, etc. is clicked to be selected, the console 7 determines the FPD cassette 2a is loaded on the bucky device 3b and applies predetermined voltage to the radiation source of the radiation generating apparatus 4b and immediately begins starting of the radiation generating apparatus 4b so that the radiation generating apparatus 4b associated with the bucky device 3b for capturing in a lying position emits radiation of a low dosage corresponding to the FPD cassette 2a. Simultaneously, the radiation generating apparatus 4b is moved so that the radiation source is positioned above the bucky device 3b for capturing in a lying position.

Alternatively, for example, when the selection screen H2 shown in FIG. 5 is displayed and the icon 3B corresponding to the bucky device 3b for capturing in a lying position displayed with a broken line is clicked to be selected, at least the FPD cassette 2a is not loaded on the bucky device 3b and the console 7 applies a predetermined high voltage from the radiation source of the radiation generating apparatus 4b and immediately begins starting of the radiation generating apparatus 4b so that the radiation generating apparatus 4b corresponding to the bucky device 3b for capturing in a lying position emits radiation with a higher voltage than a case of the FPD cassette 2a corresponding to the CR cassette 2b. Simultaneously, the radiation generating apparatus 4b is moved so that the radiation source is positioned above the bucky device 3b for capturing in a lying position.

The same can be said for when the icon 3A corresponding to the bucky device 3a for capturing in a standing position displayed with a broken line is clicked and selected on the selection screen H2 shown in FIG. 6.

In the present embodiment, in the later example, in other words, when an icon corresponding to the bucky device 3 in which the FPD cassette 2a is not loaded is selected among the icons displayed on the selection screen H2 of the display section 71, when the icon 2A corresponding to the FPD cassette 2a displayed on the display section 71 is not selected after a predetermined amount of time passes, the console 7 applies a predetermined high voltage to the radiation source of the radiation generating apparatus (in the above, radiation generating apparatus 4b) corresponding to the bucky device and controls the radiation generating apparatus so that the radiation of a dose to be set when the CR cassette 2b is loaded on the bucky device (in the above, bucky device 3b) is emitted.

In this case, the above predetermined amount of time is set to be, for example, amount of time from beginning starting of the radiation generating apparatus 4b to when the starting is finished, in other words, to a ready state.

Also, in the above case (when an icon corresponding to the bucky device 3 in which the FPD cassette 2a is not loaded is selected among the icons displayed on the selection screen H2 of the display section 71), when any one or more of the icon 2A corresponding to the FPD cassette 2a displayed on the display section 71 is selected before the above predetermined amount of time passes, the console 7 switches the voltage applied to the radiation source from a predetermined high voltage for the CR cassette to the lower predetermined voltage for the FPD cassette, and continues the starting of the radiation generating apparatus.

As described above, in a case where the FPD cassette 2a is used, successive capturing and moving image capturing in which radiation is emitted successively to the object is possible, however, in a case where the CR cassette 2b is used, when the radiation is emitted successively, the object is multiply exposed. Therefore, in the present embodiment, when voltage for the FPD cassette 2a is applied to the radiation source of the radiation generating apparatus in starting, the console 7 permits setting of successive capturing and moving image capturing on the setting screen which is not shown, however, when high voltage for the CR cassette 2b is applied, the setting of successive capturing and moving image capturing is not permitted. Specifically, when setting of successive capturing or moving image capturing is performed in such case, for example, a warning is given by audio.

When the CR cassette 2b is already loaded on the bucky device 3 corresponding to the icon selected on the selection screen H2 shown in FIG. 5 or FIG. 6, and the icon 2A corresponding to the FPD cassette 2a is selected before the above described predetermined amount of time passes, a warning is given by audio that the CR cassette 2b is already loaded on the bucky device 3.

It is possible to make a configuration in a case where an icon corresponding to the bucky device 3 in which the FPD cassette 2a is not loaded is selected on the selection screen H2, and the icon 2A corresponding to the FPD cassette 2a is selected before the above predetermined amount of time passes, a warning is given when the operator makes an instruction to emit radiation from the radiation generating apparatus 4 corresponding to the bucky device 3 before loading the FPD cassette 2a in the bucky device 3, when the CR cassette 2b is loaded on the bucky device 3 by mistake, or the like, and this is performed as necessary.

Also, although illustration is omitted, when the portable radiation generating apparatus 4c (see FIG. 1) is configured to start by the operation of the console 7, for example, it is preferable to display an icon corresponding to the portable radiation generating apparatus 4c on the selection screen H2. With such display, similar to the above described case of the icon operation of the bucky device 3 when the FPD cassette 2a is not loaded, after the icon corresponding to the portable radiation generating apparatus 4 is selected, it is possible to adjust the voltage applied to the radiation source of the portable radiation generating apparatus 4c to the predetermined voltage for the CR cassette or the FPD cassette according to whether or not the FPD cassette 2a is selected within the predetermined amount of time.

When the radiation generating apparatus 4 to emit radiation is started properly according to the type of cassette 2 to be used and is in a ready state, the operator performs the radiation image capturing according to normal procedure. In other words, alignment of the bucky device 3 loaded with the cassette 2 or the cassette 2 by itself is performed by suitably positioning the patient M (see FIG. 1) or adjusting the position of the bucky device 3 or the cassette 2 by itself and the console 7 is operated to emit radiation from the radiation generating apparatus 4.

Then, when the cassette 2 is the CR cassette 2b, as described above, the CR cassette 2b is brought to the reading device to read the image data and the image data is transmitted to the console 7 and stored in the storage section 9.

Also, when the cassette 2 is the FPD cassette 2a, and is loaded on the bucky device 3, after the capturing is finished, one or a plurality of pieces of the image data temporarily stored in the storage section of the FPD cassette 2a is transmitted to the console 7 through the bucky device 3 and stored in the storage section 9.

Also, when the cassette 2 is the FPD cassette 2a and is used by itself without loading in the bucky device 3, after the capturing is finished, one or the plurality of pieces of image data temporarily stored in the storage section of the FPD cassette 2a is transmitted from the antenna device 24 (see FIG. 2) and transmitted to the console 7 by wireless communication through the wireless access point 5.

Needless to say, when the cassette 2 is the FPD cassette 2a, the image data can be transmitted to the console 7 simultaneously with the reading out directly after finish of capturing without temporarily storing the image data in the storage section.

As described above, according to the radiation image capturing system 1 of the present embodiment, with the operation of the icons on the selection screen H2 of the display section 71 of the console 7, when the bucky device 3 loaded with the FPD cassette 2a is selected, the radiation generating apparatus 4 associated with the bucky device 3 in advance is controlled so that the radiation of the emission amount to be emitted when the FPD cassette 2a is loaded is emitted, and when the bucky device 3 in which the FPD cassette 2a is not loaded is selected, the radiation generating apparatus 4 associated with the bucky device 3 in advance is controlled so that the radiation of the emission amount to be emitted when the CR cassette 2b is loaded is emitted, and consequently, the system is configured so that the radiation generating apparatus 4 is controlled so that a different emission amount of radiation is emitted from the radiation generating apparatus 4.

Therefore, in a capturing environment where, for example, both the FPD cassette 2a and the CR cassette 2b are formed in the JIS standard size of the screen/film cassette so that both the FPD cassette 2a and the CR cassette 2b can be loaded on the same bucky device 3, a radiological technologist, doctor, etc. does not have to set the emission condition of the radiation generating apparatus 4 according to the type of the cassette 2 loaded on the bucky device 3 and suitable setting is possible automatically by only performing operation of the icon on the selection screen H2 of the display section 71 of the console 7.

Also, therefore, the operation of the radiation image capturing becomes very simple and at the same time, it is possible to effectively prevent the operator from setting the capturing condition of the cassette 2 of a type different from the type of cassette 2 loaded on the bucky device 3 and it is possible to effectively prevent increasing the total exposure amount of the patient by performing capturing again.

Further, as shown in the present embodiment, by beginning the starting of the radiation generating apparatus 4 corresponding to the bucky device 3 immediately at the step when the bucky device 3 is selected by the icon operation on the selection screen H2 of the display section 71 of the console 7, the radiation image capturing can begin promptly.

Second Embodiment

In the second embodiment, a radiation image capturing system 1 is described configured including a warning section to give a warning when the operator sets the capturing condition and the capturing condition to be set and the type of cassette to be used in the capturing do not match in the above described radiation image capturing system 1.

The configuration of the cassette 2 (FPD cassette 2a and CR cassette 2b), bucky device 3, radiation generating apparatus 4, wireless access point 5, tag reader 6, console 7, etc. composing the radiation image capturing system 1 of the present embodiment is similar to that of the radiation image capturing system 1 of the first embodiment shown in FIG. 1, and the configuration is described with the same reference numerals applied to the components which are the same as those of the first embodiment.

In the present embodiment, the console 7 is provided with a warning section 10 (see FIG. 1) such as a speaker and also the above described audio section provided in the operation section 31 of the bucky device 3 also functions as the warning section.

Further, in the present embodiment, the console 7 judges whether or not to give a warning from the warning section 10. Below, the process of making an accurate warning when it is judged that the cassette loaded on the bucky device 3 is not suitable based on the capturing order information is described with reference to the screen displayed on the display section 71 of the console 7 and also, the operation of the radiation image capturing system 1 of the present embodiment is described.

The management of the FPD cassette 2a brought into the front room R2 and the capturing room R1 with the console 7, obtainment of the capturing order information from the storage section 9 (or HIS/RIS) of the console 7 in capturing of the radiation image, display of the capturing order information on the selection screen H1 (see FIG. 4) of the display section 71 is similar to that of the first embodiment.

Figure 7:
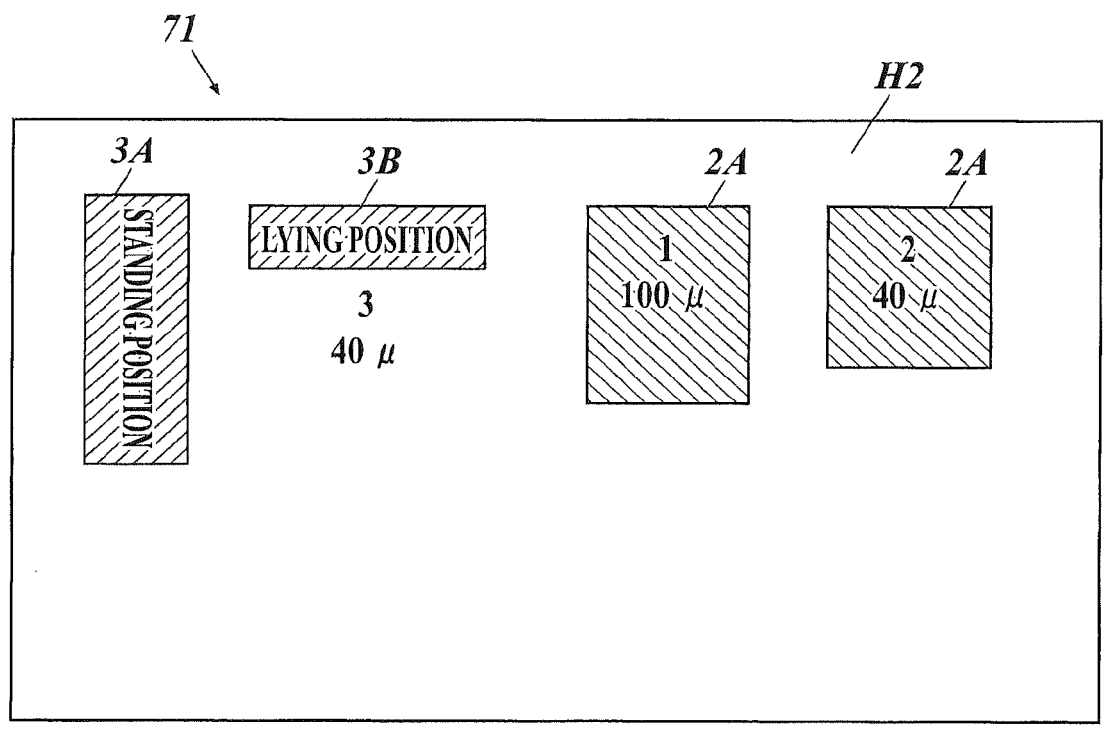
FIG. 7 is a diagram showing an example of a selected image displayed with the icon of the bucky device and the FPD cassette displayed on the display section of the console according to the second embodiment.
Figure 8:
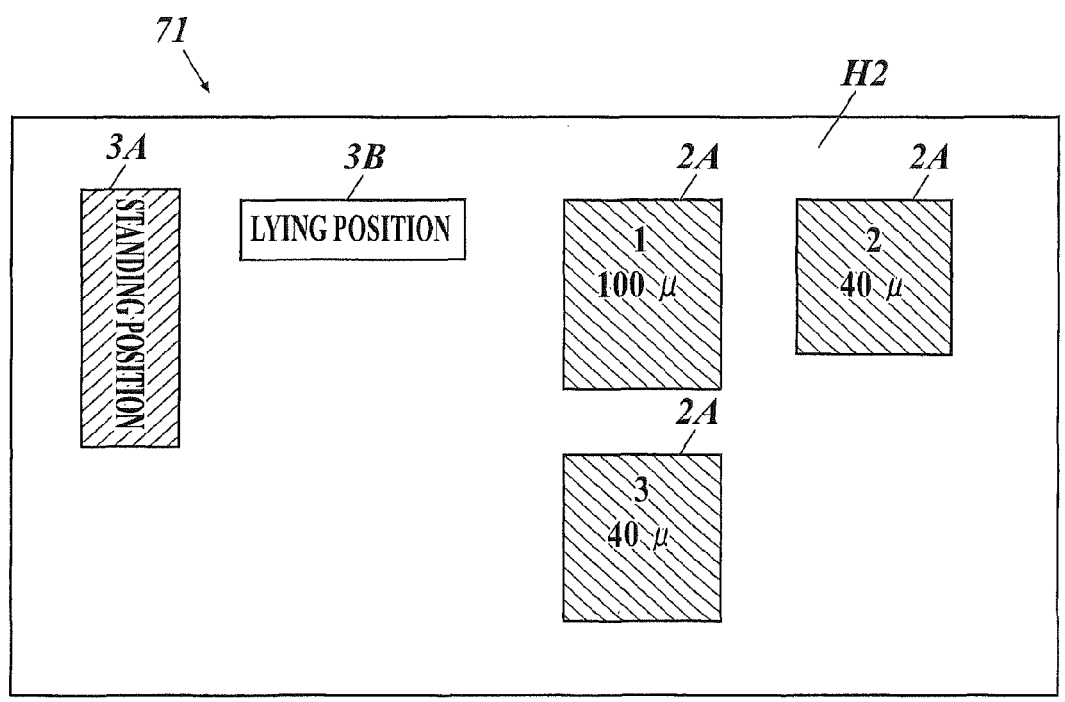
FIG. 8 is a diagram showing an example of a selected image displayed with the icon of the bucky device and the FPD cassette displayed on the display section of the console according to the second embodiment.

Then, when the capturing order information of the capturing performed this time is selected by clicking the select button h12 corresponding to the capturing order information and clicking the enter button h13, the screen on the display section 71 switches and next the console 7 displays icons as shown in, for example FIG. 7 and FIG. 8 on the selection screen H2 of the display section 71.

As shown in FIG. 7 and FIG. 8, on the left side of the selection screen H2, the icons 3A and 3B corresponding to the bucky device 3a for capturing in a standing position and the bucky device 3b for capturing in a lying position are each displayed in a state where the description of "standing position" and "lying position" are surrounded by a rectangular border line. On the right side of the selection screen H2, the icons 2A corresponding to the FPD cassettes 2a in the capturing room R1 and the front room R2 are displayed in a rectangular border line with a number 1 to 3 attached to each icon 2A.

In the present embodiment, when the cassette ID, etc. of the FPD cassette 2a is associated to the ID of the bucky device 3, the console 7 displays the icon corresponding to the bucky device 3 colored with a predetermined color such as orange (see "lying position" 3B shown in FIG. 7) and displays that the FPD cassette 2a is loaded on the bucky device 3. When the ID of the cassette of the CR cassette 2b is associated to the ID of the bucky device 3, the console 7 displays each icon corresponding to the bucky device 3 colored with a predetermined different color such as green (see "standing position" 3A shown in FIG. 7 and FIG. 8) and displays that the CR cassette 2b is loaded on the bucky device 3. FIG. 8 displays the number, resolution, etc. of the FPD cassette 2a loaded on the bucky device 3b for capturing in a lying position near the icon 3B of the "lying position".

When the ID of the FPD cassette 2a or the ID of the CR cassette 2b is not associated to the ID of the bucky device 3, the console 7 displays the inside of the border line of the icon corresponding to the bucky device 3 without color (see "lying position" 3B shown in FIG. 8) and displays that at least the cassette 2 is not loaded on the bucky device 3.

As described above, in the present embodiment, the console 7 displays each icon corresponding to the bucky device 3 displayed on the displaying section 71 in a different manner according to whether the cassette loaded on the bucky device 3 is the FPD cassette 2a or the CR cassette 2b or whether or not the cassette is loaded based on the notification from the bucky device 3.

Also, the console 7 refers to the memory and reads out the information such as resolution associated to each cassette ID of the FPD cassette 2a in the capturing room R1 and the front room R2, associates the number (1 to 3 shown in FIG. 7 and FIG. 8) attached to each cassette ID with the information such as resolution and displays the above information in the border line of the icons 2A corresponding to the FPD cassettes 2a displayed on the right side of the selection screen H2. It is possible to further display the size, etc. of the FPD cassette 2a.

For example, in a case where the operator loads the FPD cassette 2a with the number 3 on the bucky device 3b for capturing in a lying position to perform radiation image capturing, when the FPD cassette 2a with the number 3 is loaded on the bucky device 3b for capturing in a lying position in a state where the selection screen H2 shown in FIG. 8 is displayed, the selection screen H2 switches from the selection screen H2 shown in FIG. 8 to selection screen H2 shown in FIG. 7. When the FPD cassette 2a with the number 3 is loaded on the bucky device 3 for capturing in a lying position in advance, the selection screen H2 shown in FIG. 7 is displayed from the beginning when the selection screen H1 shown in FIG. 4 switches to the selection screen H2.

In this state, for example, when the selection screen H2 shown in FIG. 7 is displayed and the icon 3A corresponding to the bucky device 3a for capturing in a standing position is clicked to be selected, the console 7 determines the CR cassette 2b is loaded on the bucky device 3a.

As described above, successive capturing and moving image capturing in which radiation is emitted successively to the object is possible, however, in a case where the CR cassette 2b is used, when the radiation is emitted successively the object is multiply exposed. Therefore, when the operator sets successive capturing or moving image capturing in the next operation even when the CR cassette 2b with which successive capturing and moving image capturing cannot be performed as described above is selected, since the type of cassette loaded on the selected bucky device 3a (in this case CR cassette 2b) and the set capturing condition (in this case successive capturing or moving image capturing) do not match, the console 7 gives a warning such as audio from the warning section 10.

In the present embodiment, the audio section (warning section) of the operation section 31 of the bucky device 3 described above also gives a warning so that the warning reaches the capturing room R1. The warning section may be provided only on the bucky device 3 side.

Also, when the icon corresponding to the bucky device 3 in which the FPD cassette 2a is loaded is clicked and selected, and the capturing condition for the CR cassette 2b is set, similar to the above, since the type of cassette loaded on the selected bucky device 3 (FPD cassette 2a) does not match the set capturing condition, a warning is given from the warning section 10. In this case, compared to the normal (optimum) emission amount, the amount becomes excessive, however in most cases, the captured image can be used in diagnosis by performing suitable image processing, and for example as a response to emergency, the configuration can be made so that after the warning, the operator permits the capturing by operation.

When the radiation generating apparatus 4 to emit radiation is started properly according to the type of cassette 2 used and is in a ready state, the operator performs the radiation image capturing according to normal procedure. In other words, alignment of the bucky device 3 loaded with the cassette 2 or the cassette 2 by itself is performed by suitably positioning the patient M (see FIG. 1) or adjusting the position of the bucky device 3 or the cassette 2 by itself and the console 7 is operated to emit radiation from the radiation generating apparatus 4.

Then, when the cassette 2 is the CR cassette 2b, as described above, the CR cassette 2b is brought to the reading device to read the image data and the image data is transmitted to the console 7 and stored in the storage section 9.

Also, when the cassette 2 is the FPD cassette 2a, and is loaded on the bucky device 3, after the capturing is finished, one or a plurality of pieces of the image data temporarily stored in the storage section of the FPD cassette 2a is transmitted to the console 7 through the bucky device 3 and stored in the storage section 9.

Also, when the cassette 2 is the FPD cassette 2a and is used by itself without loading in the bucky device 3, after the capturing is finished, one or the plurality of pieces of image data temporarily stored in the storage section of the FPD cassette 2a is transmitted from the antenna device 24 (see FIG. 2) and transmitted to the console 7 by wireless communication through the wireless access point 5.

Needless to say, when the cassette 2 is the FPD cassette 2a, the image data can be transmitted to the console 7 simultaneously with the reading out directly after finish of capturing without temporarily storing the image data in the storage section.

According to the radiation image capturing system 1 of the present embodiment, in an environment where both of the FPD cassette 2a and the CR cassette 2b are formed in the JIS standard size of the screen/film cassette so that the FPD cassette 2a and the CR cassette 2b can be loaded on the same bucky device 3, in a case where an operator such as a radiological technologist, doctor, etc. sets a capturing condition such as successive capturing, moving image capturing, etc. when the CR cassette 2b is loaded on the bucky device 3, or the capturing condition for the CR cassette 2b is set with the FPD cassette 2a loaded on the bucky device 3, it is possible to judge that the type of cassette 2 loaded on the selected bucky device 3 does not match the set capturing condition and to give a warning.

Therefore, the operation of the radiation image capturing becomes very easy and at the same time, it is possible to automatically and accurately prevent the radiation image capturing to be performed using an unsuitable cassette when the operator sets the capturing condition of a type of cassette 2 different from the type of cassette 2 loaded on the bucky device 3, and it is possible to effectively prevent performing capturing again and increasing the amount of the total exposure amount of the patient.

Third Embodiment

In the second embodiment, a case where the capturing condition is set after each icon (see FIG. 7 and FIG. 8) displayed on the selection screen H2 of the display section 71 of the console 7 is clicked and the bucky device 3 or FPD cassette 2a is selected is described. Alternatively, a configuration in which the capturing condition is set in the capturing order information in advance is possible. Below, the above is described in the third embodiment of the present invention.

In the configuration of the radiation image capturing system of the present embodiment, although the processing in the console 7 is slightly different, the configuration is almost the same as that of the radiation image capturing system 1 of the above described first and second embodiment. Therefore, the member and the device including functions similar to those of the member and device in the radiation image capturing system 1 of the first and second embodiment are described applied with the same reference numerals as those of the first and second embodiment.

In the present embodiment, as shown in FIG. 9, the capturing order information is configured including the above described "capturing order ID" P1, patient information P2 to P6 and capturing information P7, P8 and further includes information of "mode of capturing" P9 as the capturing condition. As shown in FIG. 10, the capturing order information including information of "mode of capturing" P9 which is the capturing condition is displayed on the selection screen H1 of the display section 71 of the console 7.

Here, as the capturing order information to perform capturing this time, for example, when the select button h12 corresponding to the capturing order information with the capturing order ID "010" is clicked and the enter button h13 is clicked and selected, the console 7 stores the "dynamic capturing" set in the capturing order information as the capturing condition.

Then, the screen on the display section 71 switches and the selection screen H2 shown in, for example, FIG. 7 is displayed. FIG. 7 shows a state in which the CR cassette 2b is loaded on the bucky device 3a for capturing in a standing position and the FPD cassette 2a is loaded on the bucky device 3b for capturing in a lying position as described above.

In this state, when the icon 3A corresponding to the bucky device 3a for capturing in a standing position is clicked and selected, the console 7 determines the CR cassette 2b is loaded on the bucky device 3a. However, as described above, when "dynamic capturing" (moving image capturing) is set as the capturing condition in this case, multiple exposure occurs when the radiation is emitted successively when using the CR cassette 2b. Therefore, in this case, in the step where the icon of the bucky device 3a loaded with the CR cassette 2b is clicked on the selection screen H2 shown in FIG. 7, the console 7 determines that the type of cassette loaded on the selected bucky device 3 (in this case CR cassette 2b) does not match the set capturing condition (in this case successive capturing or moving image capturing) and immediately gives a warning from the warning section 10.

When the icon 3B corresponding to the bucky device 3b for capturing in a lying position is clicked and selected, the console 7 determines the FPD cassette 2a is loaded on the bucky device 3b and in this case, a warning is not given from the above described warning section 10. However, when a capturing condition for the CR cassette 2b is set later, a warning is given similar to the second embodiment. Also, when the icon 3B for the lying position is selected on the selection screen shown in FIG. 8, since the cassette is not loaded, a warning is given, but when either of the icon 2A of the FPD cassette 2a is selected after selection of the icon 3B, it is presumed from the selection that the FPD cassette is to be loaded to perform capturing, and the warning stops.

Alternatively, as the capturing order information to perform capturing, for example, when the select button h12 corresponding to the capturing order information with the capturing order ID "001" is clicked and the enter button h13 is clicked and selected, the console 7 stores "simple" set in the capturing order information as the capturing condition.

When the capturing condition is "simple", either the FPD cassette 2a or the CR cassette 2b can be used. Therefore, even if either icon 3A corresponding to the bucky device 3a for capturing in a standing position or icon 3B corresponding to the bucky device 3b for capturing in a lying position is clicked on the selection screen H2 shown in FIG. 7, a warning from the warning section 10 is not given.

As described above, according to the radiation image capturing system of the present embodiment, similar to the above described radiation image capturing system 1 of the second embodiment described above, a warning is given when the type of cassette loaded on the selected bucky device 3 does not match the set capturing condition so that radiation image capturing with an unsuitable cassette can be prevented automatically and accurately.

Also, since the capturing condition is set in the capturing order information in advance, it is possible to determine whether or not the type of cassette loaded on the selected bucky device 3 matches the set capturing condition in the step when the icon displayed on the display section 71 of the console 7 is clicked and selected and when there is no match, it is possible to immediately give a warning from the warning section 10.

In the above described first to third embodiments, two types of control are described where a high voltage for the CR cassette or a lower voltage for the FPD cassette is applied to the radiation source of the radiation generating apparatus 4, however, a configuration is possible in which finer adjustments are made.

For example, it is preferable that the emission amount of the radiation emitted from the radiation generating apparatus 4 to the patient M is adjusted as necessary depending on the body part of the captured patient M or whether the patient M is an adult or child, or whether the patient M is fat or thin, or the like. Therefore, it is preferable that fine adjustment of the emission amount is performed from the standard voltage set depending on the CR cassette or the FPD cassette as described above, by referring to the above described finer capturing condition included in the capturing order information when the console 7 sets the emission amount of the radiation emitted from the radiation generating apparatus 4.

Also, in the above described first to third embodiments, an example where the capturing order information stored in the storage section 9 of the console 7 in advance is read out or the capturing order information made in advance is obtained through the network from HIS/RIS, etc. is described, however, the capturing order information does not necessarily have to be made before the radiation image capturing and a configuration is possible where the capturing order information is made associated with the obtained image data after the radiation image capturing.

In this case, for example, the display on the selection screen H1 of the capturing order information as shown in FIG. 4 or FIG. 10 is omitted, and it is configured so that the operator operates the console 7 and displays the selection screen H2 shown in FIG. 5 to FIG. 8 on the display section 71 to perform icon operation.

Further, in the above described first to third embodiments, an example where the bucky device 3a for capturing in a standing position and the bucky device 3b for capturing in a lying position are provided as the bucky device 3 is described, however, the present invention is applied when one, or three or more bucky device 3 is provided. Needless to say, the present invention is not limited to the above described embodiments, and can be suitably modified.

INDUSTRIAL APPLICABILITY

The present invention can be used in the field of medicine in a radiation image capturing system for capturing a radiation image for diagnosis.

DESCRIPTION OF REFERENCE NUMERALS 1 radiation image capturing system
2 cassette
2a portable FPD cassette (FPD cassette)
2b CR cassette
2A icon corresponding to portable FPD cassette
3 bucky device
3A, 3B icon corresponding to bucky device
4 radiation generating apparatus
7 console
9 storage section
10 warning section
71 display section
M patient

The invention claimed is:

1. A radiation image capturing system comprising:
a radiation generating apparatus to emit radiation;
a FPD cassette which can capture a plurality of radiation images of an object successively;
a CR cassette which can store a radiation image of an object;
a bucky device associated with the radiation generating apparatus; and
a console including a display section to display an icon corresponding to the FPD cassette and an icon corresponding to the bucky device, the console being structured to communicate with the FPD cassette, the radiation generating apparatus, and the bucky device,
wherein the radiation generating apparatus is structured so that a capturing condition for radiation image capturing using the CR cassette is set when the icon of the bucky device without the FPD cassette is selected, and the capturing condition for radiation image capturing using the CR cassette is changed to the capturing condition for radiation image capturing using the FPD cassette when the icon of the FPD cassette is selected or the icon corresponding to the bucky device with the FPD cassette is selected.

2. The radiation image capturing system of claim 1, wherein the FPD cassette is compatible with the CR cassette in size.

* * * * *